US006537755B1

(12) United States Patent
Drmanac

(10) Patent No.: US 6,537,755 B1
(45) Date of Patent: Mar. 25, 2003

(54) SOLUTION-BASED METHODS AND MATERIALS FOR SEQUENCE ANALYSIS BY HYBRIDIZATION

(76) Inventor: Radoje T. Drmanac, 850 E. Greenwich Pl., Palo Alto, CA (US) 94303

( * ) Notice: Subject to any disclaimer, the term of this patent is extended or adjusted under 35 U.S.C. 154(b) by 0 days.

(21) Appl. No.: 09/536,217

(22) Filed: Mar. 27, 2000

Related U.S. Application Data

(63) Continuation-in-part of application No. 09/277,383, filed on Mar. 25, 1999.
(51) Int. Cl.[7] .......................... C12Q 1/68; C07H 21/04; C07H 21/02; C12P 19/34
(52) U.S. Cl. ...................... 435/6; 435/91.1; 435/91.52; 536/23.1; 536/24.32; 935/77; 935/78
(58) Field of Search .................... 435/6, 91.2, 91.1; 536/24.3, 24.33; 935/77, 78

(56) References Cited

U.S. PATENT DOCUMENTS

| | | | |
|---|---|---|---|
| 5,202,231 A | 4/1993 | Drmanac et al. | 435/6 |
| 5,492,806 A | 2/1996 | Drmanac et al. | 435/5 |
| 5,503,980 A | 4/1996 | Cantor | 435/6 |
| 5,525,464 A | 6/1996 | Drmanac et al. | 435/6 |
| 5,667,972 A | 9/1997 | Drmanac et al. | 435/6 |
| 5,695,940 A | 12/1997 | Drmanac et al. | 435/6 |
| 5,770,455 A | 6/1998 | Cargill et al. | 436/518 |
| 5,795,782 A | 8/1998 | Church | 436/2 |
| 5,861,250 A | 1/1999 | Stanley et al. | 435/6 |
| 5,972,619 A | 10/1999 | Drmanac et al. | 435/6 |
| 6,018,041 A | 1/2000 | Drmanac et al. | 536/24.3 |
| 6,022,686 A | 2/2000 | Garman et al. | 435/6 |
| 6,025,136 A | 2/2000 | Drmanac et al. | 435/6 |
| 6,232,064 B1 * | 5/2001 | Grotendorst et al. | 435/6 |

FOREIGN PATENT DOCUMENTS

| | | |
|---|---|---|
| WO | WO 98/31836 | 7/1923 |
| WO | WO 99/09217 | 2/1928 |
| WO | WO 95/09248 | 4/1995 |
| WO | WO 00/34527 | 6/2000 |

OTHER PUBLICATIONS

*Stratagene Catalog, Gene Characterization Kits*, p. 39, column 1, 1988.*
Broude et al., "Enhanced DNA sequencing by hybridization," *Proc. Natl. Acad. Sci. USA*, 91:3072–3076.
Drmanac et al., "Sequencing of Megabase Plus DNA by Hybridization: Theory of the Method" *Genomics*, 4, 114–128 (1989).
Drmanac et al., "An Algorithm for the DNA Sequence Generation from k–Tuple Word Contents of the Minimal Number of Random Fragments" *J. Biomol. Struct. Dyn.*, 5, 1085–1101 (1991).
Drmanac et al., "W (A or T) Sequences as Probes and Primers Suitable for Genomic Mapping and Fingerprinting" *Nucl. Acids Res.*, 19, 5839–5842 (1991).
Drmanac et al., "Sequencing by Hybridization (SBH) with Oligonucleotide Proves as an integral Approach for the Analysis of Complex Genomes" *Int. J. Genome Res.*, 1, 59–79 (1992).
Drmanac et al., "DNA Sequence Determination by Hybridization: A Strategy for Efficient Large–Scale Sequencing" *Science*, 260, 1649–1652 (1993).
Dyer et al., "The probability of unique solutions of sequencing by hybridization", *Journal of Computational Biology* 1 (2):105–110 (1994).
Guarnieri et al., Making DNA Add *Science* 273:220–223 (1996).
Kong et al., "Nanotube Molecular Wires as Chemical Sensors" *Science*, 287:622–625 (2000).
Lehrach et al., "Hybridization Fingerprinting in Genome Mapping and Sequencing" *Genome Analysis*: Genetic and Physical Mapping, 1, 39–81, Cold Spring Harbor Laboratory Press (1990).
Matthews et al., "Analytical strategies for the use of DNA probes," *Analytical Biochemistry*, 169:1–25 (1988).
Meller et al., "Rapid Nanopore Discrimination Between Single Polynucleotide Molecules" *Proc. Nat'l Acad. Sci.*, 97:1079–1084 (2000).
Nizetic et al., "An improved bacterial colony lysis procedure enables direct DNA hybridisation using short (10, 11 bases) oligonucleotides to cosmids" *Nucl. Acids Res.*, 19, 182 (1991).
Ouyang et al., "DNA Solution of the Maximal Clique Problem" *Science* 278:446–449 (1997).
Schultz et al., "Single–target molecule detection with non-bleaching multicolor optical immunolabels" *Proc. Nat'l Acad. Sci.*, 97:996–1001 (2000).
Strezoska et al., "DNA sequencing by hybridization: 100 bases read by a non–gel–based method" *Proc. Nat3 l Acad. Sci.* (USA), 88, 10089–10093 (1991).

* cited by examiner

*Primary Examiner*—Jeffrey Fredman
*Assistant Examiner*—Arun Kr. Chakrabarti
(74) *Attorney, Agent, or Firm*—Marshall, Gerstein & Borun

(57) ABSTRACT

Novel solution-based methods and materials, including apparatus, for sequence analysis by hybridization are provided.

37 Claims, 1 Drawing Sheet

SOLUTION-BASED METHODS AND MATERIALS FOR SEQUENCE ANALYSIS BY HYBRIDIZATION

This application is a continuation-in-part of U.S. application Ser. No. 09/277,383 filed Mar. 25, 1999, incorporated herein by reference.

FIELD OF THE INVENTION

The invention relates generally to novel methods and materials for nucleic acid sequence analysis by hybridization, in which the hybridization reaction occurs in a solution environment.

BACKGROUND

The rate of determining the sequence of the four nucleotides in nucleic acid samples is a major technical obstacle for further advancement of molecular biology, medicine, and biotechnology. Nucleic acid sequencing methods which involve separation of nucleic acid molecules in a gel have been in use since 1978. The other proven method for sequencing nucleic acids is sequencing by hybridization (SBH).

The traditional method of determining a sequence of nucleotides (i.e., the order of the A, G, C and T nucleotides in a sample) is performed by preparing a mixture of randomly terminated, differentially labeled nucleic acid fragments by degradation at specific nucleotides, or by dideoxy chain termination of replicating strands. Resulting nucleic acid fragments in the range of 1 to 500 bp are then separated on a gel to produce a ladder of bands wherein the adjacent samples differ in length by one nucleotide.

SBH does not require single base resolution in separation, degradation, synthesis or imaging of a nucleic acid molecule. Using mismatch discriminative hybridization of short oligonucleotides K bases in length, lists of constituent K-mer oligonucleotides may be determined for target nucleic acid. Sequence for the target nucleic acid may be assembled by uniquely overlapping scored oligonuclcotides.

There are several approaches available to achieve sequencing by hybridization. In a process called SBH Format 1, nucleic acid samples are arrayed, and labeled probes are hybridized with the samples. Replica membranes with the same sets of sample nucleic acids may be used for parallel scoring of several probes and/or probes may be multiplexed. Nucleic acid samples may,be arrayed and hybridized on nylon membranes or other suitable supports. Each membrane array may be reused many times. Format 1 is especially efficient for batch processing large numbers of samples.

In SBH Format 2, probes are arrayed at locations on a substrate which correspond to their respective sequences, and a labeled nucleic acid sample fragment is hybridized to the arrayed probes. In this case, sequence information about a fragment may be determined in a simultaneous hybridization reaction with all of the arrayed probes. For sequencing other nucleic acid fragments, the same oligonucleotide array may be reused. The arrays may be produced by spotting or by in situ synthesis of probes.

In Format 3 SBH, two sets of probes are used. In one embodiment, a set may be in the form of arrays of probes with known positions, and another, labeled set may be stored in multiwell plates. In this case, target nucleic acid need not be labeled. Target nucleic acid and one or more labeled probes are added to the arrayed sets of probes. If one attached probe and one labeled probe both hybridize contiguously on the target nucleic acid, they are covalently ligated, producing a detected sequence equal to the sum of the length of the ligated probes. The process allows for sequencing long nucleic acid fragments, e.g. a complete bacterial genome, without nucleic acid subcloning in smaller pieces.

However, to sequence long nucleic acids unambiguously, SBH involves the use of long probes. As the length of the probes increases, so does the number of probes required to generate sequence information. Each 2-fold increase in length of the target requires a one-base increase in the length of the probe, resulting in a four-fold increase in the number of probes required (the complete set of all possible sequences of probes of length k contains $4^k$ probes). For example, sequencing 100 bases of DNA requires 16,384 7-mers; sequencing 200 bases requires 65,536 8-mers; 400 bases, 262,144 9-mers; 800 bases, 1,048,576 10-mers; 1600 bases, 4,194,304 11-mers; 3200 bases, 16,777,216 12-mers; 6400 bases, 67,108,864 13-mers; and 12,800 bases requires 268,435,456 14-mers.

Because a limited number of probes can be scored in each array-based hybridization reaction, use of an extremely large number of probes requires carrying out multiple hybridization reactions.

An improvement in SBH that increases efficiency and reduces the number of hybridization reactions would greatly enhance the practical ability to sequence long pieces of polynucleotides de novo. Such an improvement would, of course, also enhance resequencing and other applications of SBH. Thus, there remains a need for additional and improved methods and materials for performing sequence analysis by hybridization.

SUMMARY OF THE INVENTION

The present invention provides novel methods and materials, including apparatus and kits, for performing sequence analysis by hybridization (referred to herein as "SBH"). According to the present invention, the efficiency, sensitivity and accuracy of these methods is improved by performing the entire hybridization step in solution, preferably coupled with single probe molecule detection. The methods and materials of the present invention advantageously allow for easier preparation of probes without attaching them to a fixed support, allow the use of larger numbers and different types of probes, improve hybridization and enzymatic kinetics relative to solid-phase hybridization (when either target or probe(s) are bound to a solid support), and allow for use of a different range of detection devices.

In one aspect, the invention provides methods of detecting a sequence of a target nucleic acid, comprising: (a) contacting a target nucleic acid with one or more mixtures of a plurality of oligonucleotide probe molecules of predetermined length and predetermined sequence, wherein each probe molecule comprises an information region and at least two probe molecules have different information regions, under conditions which produce, on average, more probe-:target hybridization with probe molecules which are perfectly complementary to the target nucleic acid in the information region of the probe molecules than with probe molecules which are mismatched in the information region, wherein the target nucleic acid is not attached to a support, and wherein the probe molecules are not attached to a support; (b) detecting probe molecules that hybridize with the target nucleic acid, using a reader capable of detecting an individual probe molecule; and (c) detecting a sequence of the target nucleic acid by overlapping sequences of the information regions of at least two of the probe molecules contacted with the target in step (a). Methods of the invention are carried out wherein at least two mixtures are contacted simultaneously, or alternatively wherein at least two mixtures are contacted sequentially. Methods of the invention include those wherein at least about 10 probe molecules distinct in their information regions, at least about 100 probe molecules distinct in their information regions, at least about 1,000 probe molecules distinct in their information regions, or at least about 10,000 probe molecules distinct in their information regions. In one aspect, methods of the invention include probe molecules that comprise modified bases.

Multiple probe molecules of the invention may also be associated with identification tags, and in one aspect, multiple probe molecules each have two identification tags. In one aspect, methods may include multiple probe molecules having the same information region which are each associated with the same identification tag. In another aspect, at least two probe molecules having different information regions are associated with different identification tags.

Methods of the invention include those wherein the probe molecules are divided into pools, wherein each pool comprises at least two probe molecules having different information regions, and all probe molecules within each pool are associated with the same identification tag which is unique to the pool. In one aspect, at least one identification tag is a bar code. Methods are provided wherein the bar code is based on a property selected from the group consisting of size, shape, electrical properties, magnetic properties, optical properties, and chemical properties. Alternatively, the identification tag is a DNA bar code comprising modified bases, a molecular bar code, or a nanoparticle bar code. In one aspect, the bar code comprises elements of varying length, each element comprising a preset number of unit tags. The preset number may vary, e.g., may be 1, 2, 3, 4, 5 or more depending on the desired number of combinations and the type of unit tags.

In another aspect, methods of the invention include a target nucleic acid which is associated with a separator tag. Alternatively, methods are provided wherein the probe molecules are associated with separator tags.

The invention further provides methods wherein before the detection step (b) described above, probe molecules that hybridize to the target nucleic acid are separated from probe molecules that do not hybridize to the target nucleic acid. In one aspect, probe molecules that do not hybridize to the target nucleic acid are eliminated by enzymatic digestion.

The invention also provides methods wherein step (b) further comprises counting the number of times probe molecules having the same information region are detected. In one aspect, the methods of the invention include a reader comprising a nanopore channel which is used to detect probe molecules in step (b). Alternatively, methods include sensing of electrical responses within or around the nanopore channel is used to detect probe molecules in step (b). In one aspect, the reader detects molecular bar codes in step (b).

The invention further provides methods wherein the probe molecules are associated with one or more tags that allow identification of 5'/3' orientation of probe molecules during detection step (b). In another embodiment, methods of the invention, the sequence of the probe molecule(s) is detected in step (b). In one aspect, methods are provided wherein at least two probe molecules are associated with identification tags and the identification tags are also detected in step (b).

The invention further provides methods of sequencing a target nucleic acid, comprising: (a) contacting a target nucleic acid with one or more mixtures of a plurality of oligonucleotide probe molecules of predetermined length and predetermined sequence, wherein each probe molecule comprises an information region and at least two probe molecules have different information regions, under conditions which produce, on average, more probe:target hybridization with probe molecules which are perfectly complementary to the target nucleic acid in the information region of the probe molecules than with probe molecules which are mismatched in the information region, wherein the target nucleic acid is not attached to a support, and wherein the probe molecules are not attached to a support; (b) covalently joining probe molecules that form contiguous probe:target hybrids that are perfectly complementary to the target in the information region of the probe molecules; and (c) detecting covalently joined probe molecules, using a reader capable of detecting an individual probe molecule. In another aspect, methods of the invention further comprise the step of: (d) detecting a sequence of the target nucleic acid by overlapping at least two sequences generated by combining sequences of the information region of two probe molecules contacted with target nucleic acid in step (a). As used herein, "combining sequences of the information region of two probe molecules" means contiguously combining sequences in proper 5'–3' orientation. In another embodiment, methods are provided wherein before detection step (c), covalently joined probe molecules are separated from probe molecules that have not been covalently joined.

Also provided are methods of the invention wherein at least one nucleotide is added to the end of one or more probe molecules that hybridize to target nucleic acid using a polymerase or active fragment thereof. In one aspect, the probe molecules are contacted with a mixture of four different uniquely labeled nucleotides.

Methods are provided wherein target nucleic acids comprising an entire human genome are contacted with probe molecules. Alternatively, methods are provided wherein a single nucleotide polymorphism is detected.

The invention further provides kits comprising a mixture of probe molecules, wherein about 100 or more probe molecules each have distinct information regions, wherein two or more of the sequences of said distinct information regions within the mixture overlap. In one aspect, the kits include about $10^5$ or less probe molecules each have the same information region. In another embodiment, the kits include about $10^4$ or less probe molecules each have the same information region. Alternatively, kits of the invention include those wherein each information region is represented by $10^4$ or more probe molecules having the same information region. Also provided are kits wherein at least two probe molecules having the same information region have the same identification tag.

In one aspect, kits are provided comprising a set of mixtures of probe molecules, wherein about 100 or more probe molecules each have distinct information regions, wherein two or more of the sequences of said distinct information regions within the set overlap. In one aspect, kits of the invention are provided wherein about $10^5$ or less probe molecules each have the same information region. In another aspect, kits are provided wherein at least two probe molecules having different information regions are in the same pool and have the same identification tag. Kits are also provided wherein about 5000 or more probe molecules each have the same information region.

The invention further provides tags which are bar codes comprising an alternating arrangement of elements of varying detectable properties, wherein consecutive elements have a difference in at least one of the detectable properties. In one aspect, the elements in the tag comprise multiple unit tags of varying detectable properties and said elements vary in length.

The present invention provides methods for analyzing the sequence of a target nucleic acid, comprising the steps of (a) contacting a target nucleic acid with a mixture of a plurality of oligonucleotide probes (which may include a plurality of probe molecules) of predetermined length and predetermined sequence, wherein each probe molecule comprises an information region, under conditions which discriminate between probe:target hybrids that are perfectly complementary in the information region of the probe and probe:target hybrids that are mismatched in the information region of the probe (i.e., under conditions which produce, on average, more probe:target hybridization with probes which are perfectly complementary to the target nucleic acid in the information region of the probes than with probes which are mismatched in the information regions), wherein the target nucleic acid is not attached to a fixed support, and wherein the probes are not attached to a fixed support; (b) detecting a subset of probes that hybridize with the target nucleic acid, preferably using a reader capable of detecting an individual probe molecule; and (c) determining the sequence of the target nucleic acid from two or more of the probes detected in step (b).

Depending on the conditions of hybridization and the use of pooling methods, described in further detail below, step (b) may include detection of more probes than the subset that hybridizes with the target nucleic acid. However, the SBH process and algorithms are very robust and can handle a large number of false positive probes, as discussed more fully in U.S. Provisional Application Ser. No. 60/115,284 filed Jan. 6, 1999, and related co-owned, co-pending U.S. application Ser. No. 09/479,608 filed Jan. 6, 2000, both of which are incorporated herein by reference.

Determining the sequence in step (c) can be done, for example, by actually overlapping the sequences of some (e.g., two or more, three or more, or four or more) or all of the detected probes for the target nucleic acid, or by comparing the detected set of probes for the target nucleic acid (which may be correlated with the identity of a nucleic acid sample to serve as a signature for identifying the nucleic acid sample) to the detected set for another target nucleic acid.

Optionally, between steps (a) and (b), a step of separating probe:target hybrids that are perfectly complementary in the information region of the probe from probe:target hybrids that are mismatched in the information region of the probe is carried out. Alternatively, between steps (a) and (b), a step of covalently joining probes that form contiguous probe:target hybrids that are perfectly complementary to the target in the information region of the probes is carried out, and in step (b) a subset of covalently joined probes is detected.

The probes may be associated with identification tags. Each of the probes may be associated with a unique identification tag; alternatively, the probes may be divided into informational pools, and all probes within each informational pool are associated with an identification tag unique to the informational pool. A preferred identification tag is a DNA bar code. The target nucleic acid or the probes may also be associated with one or more separator tags that aid separation of the probe:target hybrids from the unhybridized nucleic acids.

The number of probes used in the hybridization step may be at least about 10, at least about 100, at least about 1000, at least about $10^4$, at least about $10^5$, at least about $10^6$, or at least about $10^7$ different probes (meaning the number of probe sequences distinct in their information regions), and may potentially range up to about $10^{10}$ different probes or even more. According to this method, the mixture of probe molecules comprises at least two and preferably many more probe molecules each having different information regions.

In detection step (b), the positive probes may be detected using a reader comprising a nanopore channel. Detection may take place via, e.g., sensing of electrical responses within or around the nanopore channel as the probe molecule passes through or over the pore. In preferred embodiments of the method, a reader comprising a nanopore channel detects a DNA bar code associated with each probe, or detects the sequence of the probe itself. Alternatively, the positive probes may be detected using any suitable reader known in the art that is capable of detecting single probe molecules.

Another aspect of the invention provides an apparatus comprising means for carrying out the hybridization step and means for carrying out the detecting step, as described above. Such an apparatus preferably comprises a reader comprising a nanopore channel.

A further aspect of the invention provides sets of probes in the form of one or more kits, each set comprising a mixture of different probes. The set of probes may comprise at least about 10, 100, 1000, $10^4$, $10^5$, $10^6$, $10^7$, $10^8$, $10^9$, or $10^{10}$ different probes (meaning the number of probe sequences distinct in their information region). Preferably each information region is represented by about $10^4$ or more probe molecules (which may include degenerate ends). Each probe in the set may be associated with one or more identification tags and optionally one or more separator tags. Each probe in the set need not be associated with a unique identification tag, particularly if the kit is intended for use with pooling methods in SBH.

The improved SBH efficiency provided by the present invention is particularly advantageous for sequencing and resequencing applications that require an extremely large number of probes. Examples of applications that require very large numbers of probes are: (1) sequencing or resequencing of the entire human genome and other complex genomes, (2) sequencing or resequencing of total mRNA or cDNA in a human or other complex cell, (3) genotyping thousands or millions of single nucleotide polymorphisms in individual human genomes, (4) de novo sequencing of thousands of bases. Potentially, all of the probes that would be needed to perform these types of sequence analysis could be used in a single solution-based hybridization reaction with the target polynucleotide sequence.

The methods and materials of the invention also may be useful for carrying out DNA computing, described, for example, in Ouyang et al., Science, 278:446–9 (1997), Guarnieri et al., Science, 273:220–3 (1996).

Numerous additional aspects and advantages of the invention will become apparent to those skilled in the art upon consideration of the following detailed description of the invention which describes presently preferred embodiments thereof.

DETAILED DESCRIPTION OF THE INVENTION

Figure 1:
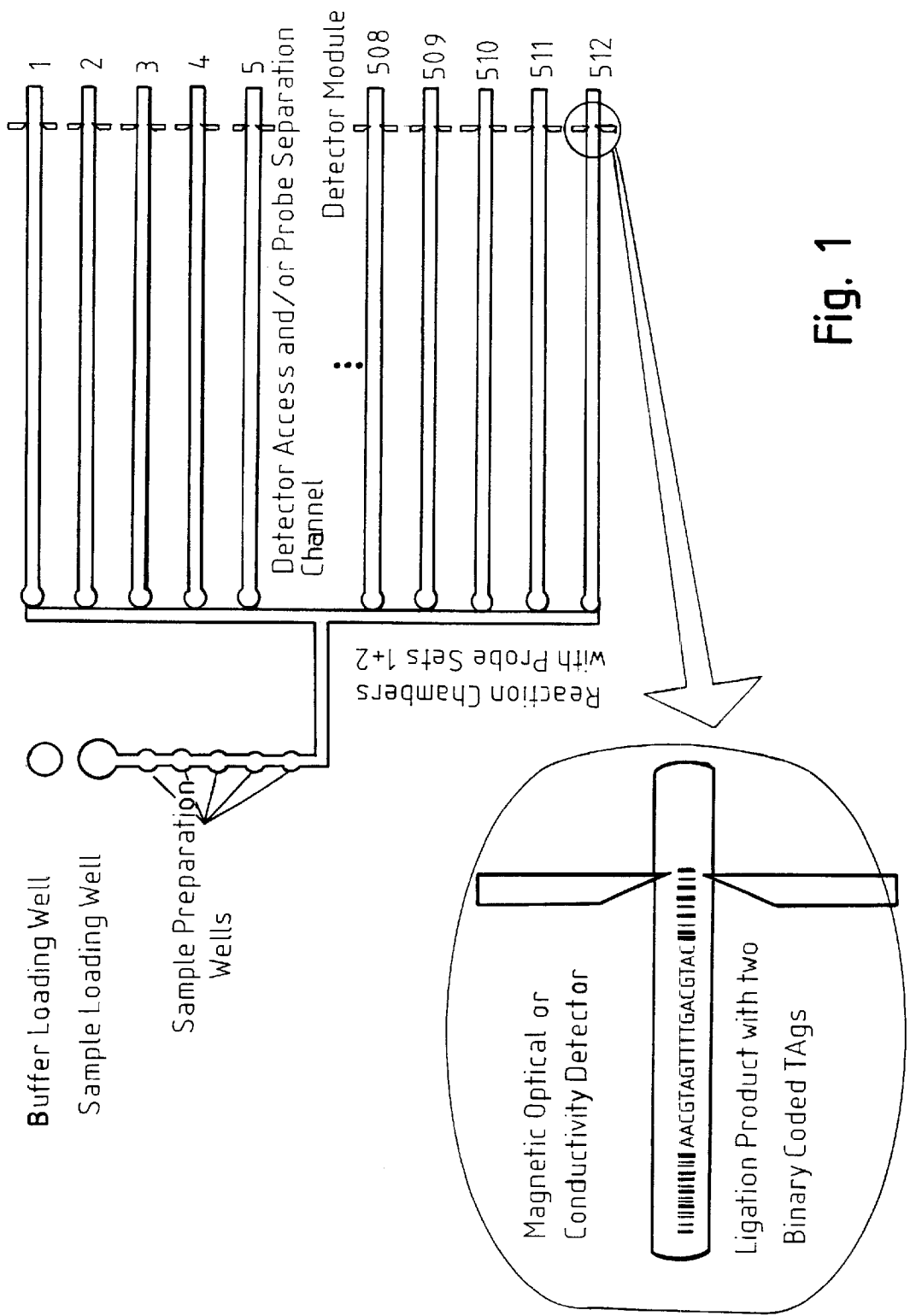
FIG. 1 shows an exemplary bar code based on magnetic, optical or conductivity properties.

The three major steps of SBH are biochemical hybridization of probes to target polynucleotide, detection of positive results (that are expected to include probes that are fully complementary to the target nucleic acid), and informational sequence analysis or assembly from the results, which may involve overlapping sequences of the information regions of the probes.

The present invention provides novel methods and materials, including apparatus, for performing SBH wherein the entire hybridization step is performed in a solution environment. The present invention provides improvements in efficiency, sensitivity and accuracy of SBH in comparison to conventional SBH methods, and can be used for any types of sequence analysis that conventional SBH methods are useful for. The procedure has many applications in nucleic acid diagnostics, forensics, and gene mapping. It also may be used to discover mutations and polymorphisms including single nucleotide polymorphisms (SNP) in a selected portion of a gene, the full gene, the entire genome, or a subset of the genome, to identify mutations responsible for genetic disorders and other traits, to verify the identity of nucleic acid fragments, to identify infectious agents, specific strains thereof, or mutants thereof (including viruses, bacteria, fungi, and parasites), to identify nucleic acid in samples for forensic purposes or for parental identification, to assess biodiversity and to produce many other types of data dependent on nucleic acid sequence. See, e.g., Examples 19 through 27 of Int'l Publication No. WO 98/31836 published Jul. 23, 1998 and WO 99/09217 published Feb. 28, 1999, both of which are incorporated herein by reference.

The SBH methods of the present invention differs from conventional SBH methods primarily because (1) the hybridization reaction is carried out entirely in solution (i.e., neither the probes nor the target nucleic acids are attached to a fixed support), (2) a mixture of a large number of probes can be hybridized to the target nucleic acid at the same time in solution, and (3) the detection of positive probes is carried out at the level of single molecules, rather than hundreds or thousands of molecules (e.g., if positive probes are detected using mass spectrometry, hybridization of perhaps a thousand probes would be required to generate a detectable signal, or alternatively if probes are radioactively labeled, hybridization of perhaps $10^5$ probes would be required to generate a detectable positive signal).

Conventional SBH is a well developed technology that may be practiced by a number of methods known to those skilled in the art. For example, variations of techniques related to sequencing by hybridization are described in the following documents, all of which are incorporated by reference herein: Drmanac et al., U.S. Pat. No. 5,202,231 (hereby incorporated by reference herein)–Issued Apr. 13, 1993; Drmanac et al., U.S. Pat. No. 5,525,464 (hereby incorporated by reference herein)—Issued Jun. 11, 1996; Drmanac, PCT Patent Appln. No. WO 95/09248 (hereby incorporated by reference); Drmanac et al., Genomics, 4, 114–128 (1989); Drmanac et al., Proceedings of the First Int'l. Conf. Electrophoresis Supercomputing Human Genome Cantor et al. eds, World Scientific Pub. Co., Singapore, 47–59 (1991); Drmanac et al., Science, 260, 1649–1652 (1993); Lehrach et al., Genome Analysis: Genetic and Physical Mapping, 1, 39–81 (1990), Cold Spring Harbor Laboratory Press; Drmanac et al., Nucl. Acids Res., 4691 (1986); Stevanovic et al., Gene, 79, 139 (1989); Panusku et al., Mol. Biol. Evol., 1, 607 (1990); Nizetic et al., Nucl. Acids Res., 19, 182 (1991); Drmanac et al., J. Biomol. Struct. Dyn., 5, 1085 (1991); Hoheisel et al., Mol. Gen., 4, 125–132 (1991); Strezoska et al., Proc. Nat'l. Acad. Sci. (USA), 88, 10089 (1991); Drmanac et al., Nucl. Acids Res., 19, 5839 (1991); and Drmanac et al., Int. J. Genome Res., 1, 59–79 (1992).

Conventional SBH approaches use arrays of target samples which are hybridized to labeled probes (Format 1), or arrays of probes which are hybridized to labeled target samples (Format 2), for efficient parallel scoring of multiple hybridization events. In one approach, either target samples or probes are attached to solid supports in the form of beads that serve to separate parallel hybridization reactions in the reading or detection step. Beads or other markers can be used as tags to identify probes. Mass spectrometry technology can also be used to distinguish probe species on the basis of their mass even when the probes are not tagged.

Format 1, 2 and 3 SBH methods are described in further detail below. In addition, a set of probes can be scored in the form of informative pools with minimal loss of information, as described in U.S. Provisional Application Ser. No. 60/115,284 entitled "Enhanced Sequencing by Hybridization Using Informative Pools of Probes" filed Jan. 6, 1999, and related co-owned, co-pending U.S. application Ser. No. 09/479,608 filed Jan. 6, 2000, both of which are incorporated herein by reference. Other types of pools may be used.

In addition, pooling probes that cannot be distinguished in the reading step is possible, and probes with unique tags can be multiplexed in the same hybridization reaction. For example, probes that are difficult to distinguish during the reading step on the basis of their sequence alone are categorized in an informative pool, wherein the entire pool is scored as positive if any one of the probes is detected. As another example, probes can be grouped and tagged as follows. Probes that are difficult to distinguish during the reading step on the basis of their sequence alone are put in a group, and each distinct probe molecule (i.e., different within its information region) within a group is attached to an identification tag that is unique within that group, although the tag may be repeated in a different group. Alternatively, probes that are easy to distinguish on the basis of sequence alone can be put in a group, and each distinct probe molecule within the group is attached to a tag common to the group. Thus, probes having very similar-appearing sequences may be distinguished on the basis of their different identification tags, while probes having very different-appearing sequences could share the same identification tag and may be distinguished on the basis of sequence alone. In this way, multiple groups could be combined together and still allow distinct probe molecules to be distinguished from each other. In another embodiment, probes that have very different-appearing sequences need not be tagged or labeled at all but are discriminated on the basis of sequence.

Probes can be individually synthesized in separate reactions or in situ, or a combination of two much smaller sets of shorter probes may be used to score a much larger set of longer probes (1024 5-mers×1024 5-mers=1,048,576 10-mers).

The length of the target sequence that can be analyzed or read (the "read length") using SBH depends on the length of the probes and the availability of additional information. For example, when a known gene is sequenced for the purpose of detecting polymorphisms or mutations in individuals, the known reference sequence will aid the sequence analysis. If the hybridization information is used alone, without any additional information, the read length for 10-mer probes is about 800 bases. The read length approximately doubles for every additional base extension of the probe length (e.g., the read length for 11-mer probes is about 1600 bases).

As the length of the probes increases, so does the number of probes required to generate sequence information. Each one-base increase in the length of the probe (providing a two-fold increase in read length) requires a four-fold increase in the number of probes required because a complete set of probes of length k contains $4^k$ probes. For example, sequencing 100 bases of DNA requires 16,384 7mers; sequencing 200 bases requires 65,536 8-mers; 400 bases, 262,144 9-mers; 800 bases, 1,048,576 10-mers; 1600 bases, 4,194,304 11-mers; 3200 bases, 16,777,216 12-mers; 6400 bases, 67,108,864 13-mers; and 12,800 bases requires 268,435,456 14-mers.

In principle, the SBH method can read the entire human genome in a single hybridization reaction if an extremely large number of long-enough probes is used. Previously available methods involving array-based or support-based hybridization, however, were limited by the number of probes that could be attached to a single array or by the number of supports that could be used at once. The present invention allows an extremely large number of probes to be hybridized in a single solution-based reaction.

According to the present invention, a set of oligonucleotide probes consisting of a very large number of different probes is allowed to hybridize to an unknown target polynucleotide or a mixture of unknown target polynucleotides in solution. The subset of probes that hybridizes to the target polynucleotide is then selected from the negative probes and analyzed by a reader that detects and discriminates individual oligonucleotide molecules. For any given target sequence, most of the probes will be negative. For example, when sequencing a 200 bp target nucleic acid with 65,536 8-mers, only about 200 probes will be scored as positive (for a single-stranded polynucleotide, or 400 probes will be scored as positive for a double-stranded polynucleotide). Thus, the actual number of probes in the positive probe subset that must be detected is relatively small in comparison to the original set of probes.

The advantages provided by the present invention are: 1) simplified preparation of pools of probes and parallel scoring of an extremely large number of probe 2) efficient hybridization and enzymatic kinetics in solution; 3) single molecule sensitivity, allowing (a) DNA analysis without PCR or other amplification reactions, (b) high accuracy by performing stringent hybridization and enzymatic or chemical elimination of mismatches, (c) scoring very large number of probes (especially when informative pools are used) with no background that might otherwise be prohibitive if probes are conventionally labeled.

The methods provided by the invention include a method comprising the steps of: (a) contacting a target nucleic acid with a mixture (or multiple mixtures) of a plurality of probes of predetermined length and predetermined sequence, wherein each probe comprises an information region, under conditions which discriminate between probe:target hybrids that are perfectly complementary in the information region of the probe and probe:target hybrids that are mismatched in the information region of the probe (i.e., under conditions which produce, on average, more probe:target hybridization with probe molecules which are perfectly complementary to the target nucleic acid in the information region of the probes than with probe molecules which are mismatched in the information regions), optionally wherein neither the target nucleic acid nor the probes are attached-to a solid support; (b) detecting a subset of probes that hybridize with the target nucleic acid, optionally including a step of separating out the positive subset of probes; and (c) determining the sequence of the target nucleic acid from two or more of the probes detected in step (b), e.g., by compiling the overlapping sequences of the detected probes, or by otherwise analyzing the detected subset of probes.

For example, the sequence of the target nucleic acid may be determined by comparing the "signature" set of detected probes (and optionally overlapping and assembling some or all of the sequences of this probe set) to that of the "signature" set of detected probes for another target nucleic acid. A variety of algorithms and other methods are known in the art for analyzing the data obtained from the detection step. See, e.g., Int'l Publication No. WO 98/31836 published Jul. 23, 1998 (especially Examples 11 through 17 and 28 through 29 of WO 98/31836) and WO 99/09217 published Feb. 28, 1999, both of which are incorporated herein by reference. Further methods for data analysis in SBH, including data analysis when pooling methods are used, and statistical analysis of overlapping probe sequences and scores.that need not involve assignment of "positive" or "negative" scores (including continuous scoring methods, rescoring methods, and maximum likelihood determination methods), are described in U.S. Provisional Application Ser. No. 60/115,284 filed Jan. 6, 1999, and related co-owned, co-pending U.S. application Ser. No. 09/479,608 filed Jan. 6, 2000, both of which are incorporated herein by reference.

The plurality of probes used in step (a) may be an extremely large number, for example, about $10^4$, $10^5$, $10^6$, $10^7$, $10^8$, $10^9$, or $10^{10}$ probes. The mixture of probe molecules comprises at least two, at least three, at least four, at least 10, at least 16, at least 32, or more probe molecules each having different information regions. In step (a) either the target nucleic acid or the probes may be attached to a solid support, but step (a) is preferably carried out when the target nucleic acid and all of the probes are in solution (i.e., not attached to a fixed support such as a membrane or array or bead). Probes are optionally attached to identification tags or separator tags as described below.

In step (b), the positive probes (probes that hybridize with the nucleic acid) may be detected while remaining in the hybridization reaction solution, or the positive probes may first be selected or separated out from the negative probes, optionally by use of associated separator tag(s), before being identified. Further detail is provided.below in the section entitled "Selection of Positive Probes."

The positive probes may be identified directly by reading their nucleotide sequence, or indirectly by detecting a unique identification tag (which may be a string of unit tags forming a composite identification tag) associated with a single probe or an identification tag associated with an informative pool of probes. Further detail on suitable readers capable of single probe molecule detection is provided below in the section entitled "Readers Used to Detect Positive Probes."

In a preferred embodiment, probes are labeled with DNA or other bar codes and are grouped in informative pools. The positive probes are selected from the negative probes, and the positive probes are detected using a reader comprising a nanopore channel.

Target Polynucleotide

"Target nucleic acid" or "target polynucleotide" refers to the nucleic acid of interest, typically the nucleic acid that is sequenced in the SBH assay. Potential target polynucleotides include naturally occurring or artificially created DNA (e.g., genomic DNA and cDNA) and RNA (e.g., mRNA), including nucleic acids used as part of DNA computing. The target nucleic acid may be composed of ribonucleotides, deoxyribonucleotides or mixtures thereof. Typically, the target nucleic acid is a DNA. While the target nucleic acid can be double-stranded, it is preferably single stranded. The "read length" of the target nucleic acid can be any number of nucleotides, depending on the length of the probes, but is typically on the order of 100, 200, 400, 800, 1600, 3200, 6400, or even more nucleotides in length, up to the entire human genome.

The target nucleic acid can be obtained from virtually any source and can be prepared using methods known in the art. For example, target nucleic acids can be isolated by PCR methodology, or by cloning into plasmids (for a convenient target nucleic acid fragment length of 500 to 5,000 base pairs), or by cloning into yeast or bacterial artificial chromosomes (for a convenient target nucleic acid fragment length of up to 100 kb);

Depending on the desired length for use in the SBH assay, the target nucleic acid may be sheared into fragments prior to use in an SBH assay. Fragmentation may be accomplished by nonspecific endonuclease digestion, restriction enzyme digestion (e.g., by Cvi JI), physical shearing (e.g., by ultrasound) or NaOH treatment. Fragments may be separated by size (e.g., by gel electrophoresis) to obtain the desired fragment length. Fragmentation of the target nucleic acid also may avoid hindrance to hybridization from secondary structure in the sample. The sizes of the target nucleic acid fragments used in the hybridization reaction optimally range in length from slightly longer than the probe length to twice the probe length, e.g., 10–100 or 10–40 bases.

Probes

"Probes" refers to relatively short pieces of nucleic acids, preferably DNA. Probes are preferably shorter than the target DNA by at least one base, and more preferably they are 25 bases or fewer in length, still more preferably 20 bases or fewer in length. Of course, the optimal length of a probe will depend on the length of the target nucleic acid being analyzed. For a target nucleic composed of about 100 or fewer bases, the probes are at least 7-mers; for a target of about 100–200 bases, the probes are at least 8-mers; for a target nucleic acid of about 200–400 bases, the probes are at least 9-mers; for a target nucleic acid of about 400–800 bases, the probes are at least 10-mers; for a target nucleic acid of about 800–1600 bases, the probes are at least 11-mers; for a target of about 1600–3200 bases, the probes are at least 12-mers, for a target of about 3200–6400 bases, the probes are at least 13-mers; and for a target of about 6400–12,800 bases, the probes are at least 14-mers. For every additional two-fold increase in the length of the target nucleic acid, the optimal probe length is one additional base. Those of skill in the art will recognize that for Format 3 SBH applications, the above-delineated probe lengths are post-ligation. Thus, as used throughout, specific probe lengths refer to the actual length of the probes for Format 1- and 2-like SBH applications and the lengths of ligated probes for Format 3 or Format 3-like SBH applications. Probes are normally single stranded, although double-stranded probes ray be used in some applications.

Probes may be prepared using standard chemistry procedures known in the art. The length "K" of the probes described above refers to the length of the informational content (i.e., the information region or the informative region) of the probes, not necessarily the actual physical length of the probes. The probes used in SBH frequently contain degenerate ends [e.g., one to three non-specified (mixed A,T,C and G) or universal (e.g. M base or inosine) bases at the ends] that aid hybridization but do not contribute to the information content of the probes. Hybridization discrimination of mismatches in these degenerate probe mixtures refers only to the length of the informational content, not the full physical length. For example, SBH applications frequently use mixtures of probes of the formula $N_xB_yN_z$, wherein N represents any of the four bases and varies for the polynucleotides in a given mixture, B represents any of the four bases but is the same for each of the polynucleotides in a given mixture, and x, y, and z are all integers. In this formula, $N_x$ and $N_z$ represent the degenerate ends of the probe and $B_y$ represents the information content of the probe (e.g., a uniquely arrayed probe in conventional SBH).

According to the present invention, a single information region may be represented by not only multiple probe molecules of exactly the same sequence but also multiple probe molecules that differ in sequence outside of the information region (e.g., degenerate ends).

The probes may consist solely of naturally-occurring nucleotides and native phosphodiester backbones, or the probes may be modified or tagged to enhance specificity of detection. For example, the probes may be composed of one or more modified bases, such as 7-deazaguanosine, or one or more modified backbone interlinkages, such as a phosphorothioate. The only requirement is that the probes be able to hybridize to the target nucleic acid. A wide variety of modified bases and backbone interlinkages that can be used in conjunction with the present invention are known, and will be apparent to those of skill in the art. For example, modified bases that are about twice the size of a conventional nucleotide are known in the art. Modifications that increase or decrease the size of the units at each base position are expected to improve the ability of some readers to discriminate the unit at each base position.

Other variations include the use of oligonucleotides to increase specificity or efficiency, cycling hybridizations to increase the hybridization signal, for example by performing a hybridization cycle under conditions (e.g. temperature) optimally selected for a first set of labeled probes followed by hybridization under conditions optimally selected for a second set of labeled probes. Shifts in reading frame may be determined by using mixtures (preferably mixtures of equimolar amounts) of probes ending in each of the four nucleotide bases A, T, C and G.

The oligonucleotide probes are preferably tagged with identification tags to enhance detection or discrimination and are optionally tagged with separator tags to aid selection, as described below in the section entitled "Selection of Positive Probes." According to one embodiment, enough identification tags are used so that each probe of distinct sequence in the information region can be tagged with a unique identification tag and so that positive probes can be identified during the reading/detection step using these identification tags. Alternatively, when informative pools of probes are used, all the probes in each informative pool are tagged with the same identification tag that is unique to the informative pool but different from other informative pools.

Examples of suitable identification tags include nanobeads or nanoparticles, polymers or molecules, which may have different size, shape, electrical (e.g., conductivity), magnetic, optical (e.g., opacity), chemical or other properties matched with the appropriate types of readers. Appropriate readers are described below in the section entitled "Readers Used to Detect Positive Probes." Preferably the identification tags are capable of being multiplexed, i.e. their properties can be varied (including by use in a bar code) to allow the preparation of multiple unique identification tags.

Nanoparticles can be of any size that is capable of detection according to the methods of the invention, but are preferably less than about 500 nm, more preferably about 1 to about 100 nm, and most preferably in the range of about 2 to about 20 nm. In one exemplary embodiment, nanoparticles can be fragments of carbon single-walled nanotubes or multi-walled nanotubes.

Nanotubes may have different diameters, between 1–2 nm for single walled nanotubes and 2–25 nm for multiwalled nanotubes. Also nanotubes may be cut to different lengths. This provides a nice system for making bar codes with elements that have alternating diameter. For example from 9 elements (nanotubes of three different diameter D1, D2, D3, and each type cut at three different lengths (L1, L2, L3). Each element may be modified at both ends with a linker that may be blocked and deblocked to allow-coupling in a process analogous to DNA synthesis. There are many different alternating orders of coupling the elements of different diameter in a chain containing N elements. For example for a chain of four elements the orders include D1-D2-D1-D2-Probe or D2-D1-D2-D1-Probe, D1-D3-D1-D3-Probe, D2-D3-D2-D3-Probe, D1-D2-D3-D1, and many others 3×2exp3; for each order 3exp4 different bar codes can be produced.

One exemplary embodiment of a label capable of single molecule detection is the use of plasmon-resonant particles (PRPs) as optical reporters, as described in Schultz et al., Proc. Nat'l Acad. Sci., 97:996–1001 (2000), incorporated herein by reference. PRPs are metallic nanoparticles, typically 40–100 nm in diameter, which scatter light elastically with remarkable efficiency because of a collective resonance of the conduction electrons in the metal (i.e., the surface plasmon resonance). The magnitude, peak wavelength, and spectral bandwidth of the plasmon resonance associated with a nanoparticle are dependent on the particle's size, shape, and material composition, as well as the local environment. By influencing these parameters during preparation, PRPs can be formed that have scattering peak anywhere in the visible range of the spectrum. For spherical PRPs, both the peak scattering wavelength and scattering efficiency increase with larger radius, providing a means for producing differently colored labels. Populations of silver spheres, for example, can be reproducibly prepared for which the peak scattering wavelength is within a few nanometers of the targeted wavelength, by adjusting the final radius of the spheres during preparation. Because PRPs are so bright, yet nanosized, they can be used as indicators for single-molecule detection; that is, the presence of a bound PRP in a field of view can indicate a single binding event.

A string of consecutive or nonconsecutive unit tags can be linked together to form a "bar code," e.g. a "molecular bar code" or a "nanoparticle bar code." A set of distinct molecules or particles may even be linked or cross-linked in various combinations to form a type of three-dimensional bar code; for example, combinations of 8 very distinct molecules can form 512 3-element chains or 32,768 5-element chains. Preferably, however, bar codes are chains containing no branches.

Bar code combinations can also be made by further grouping the unit tags into elements of varying length that each comprise multiple unit tags. In one aspect, the invention provides a bar code tag comprising an alternate arrangement of elements of varying detectable properties. Preferably, bar codes are prepared such that consecutive elements do not have the same detectable properties. In another aspect, bar code tags may include elements that comprise multiple unit tags of varying detectable properties and the elements also vary in length. For example, in a binary code that uses small (S) and large (L) unit tags, the unit tags can be grouped into short elements (of two unit tags) and long elements (of four unit tags) as follows:

| | |
|---|---|
| SS | small short element |
| SSSS | small long element |
| LL | large short element |
| LLLL | large long element |

A binary code using these elements to form $2 \times 2^4$ combinations, which would vary in length from 8 to 16 unit tags, might appear as follows:

SS-LL-SSSS-LL

LL-SSSS-LL-SS

SS-LL-SS-LL

LLLL-SSSS-LLLL-SSSS

If three different types of unit tags and three different lengths of elements are used, there are $3 \times 2^{n-1} \times 3^n$ combinations, where n is the number of elements in the bar code. The advantages of this "alternating" bar code approach are the simplification of combinatorial synthesis of the probes and bar codes because fewer steps are needed to add the elements making up the bar code.

Preferred identification tags are "DNA bar codes" that can be present at one or both ends of the probe. For example, a binary digital bar code can be formed by using a neutral base such as inosine to represent a "1" and the absence of a base (i.e., phosphodiester backbone alone) to represent a "0." The number of distinct identification tags made possible by this binary system is $2^N$, where N is the number of digits in the bar code. Alternatively, the DNA bar codes need not be limited to a binary system if artificial bases are used to provide multiple signals at each position. For example, a small modified base with a reduced number of groups can be used to signify a "1" and a larger base such as inosine or inosine with additional groups could signify a "2," thereby providing 3 options at each position. Four or more options at each base position could be provided by using molecules of different sizes, as long as the molecules are distinguishable by the reader. For example, modified bases that are about twice the size of a conventional nucleotide are known in the art. Modifications that increase or decrease the size of the units at each base position are expected to improve the ability of some readers to discriminate the unit at each base position. The advantages of using DNA bar codes are easier synthesis and detection of the probes and easier processing of the resulting information.

Similarly, combinations in a "molecular bar code" are made possible by consecutively linking molecules (other than nucleotides) of different size, shape, electrical, magnetic or other properties that can be discriminated from each other. Optionally, one end of the molecular bar code or of the probe molecule has a common tag that shows the orientation of the oligonucleotide probe molecule (i.e., an orientation marker).

Tagging of probes at both ends with identification tags may allow for identifying 5'/3' orientation of probes in reading. In addition, when a combination of two smaller sets of shorter probes is used in a Format 3-like method, which is equivalent to the use of a much larger set of longer probes (by ligating the two shorter probes together), further useful combinations of tags are generated (i.e., a new "double" tag is generated).

Bit based, or "bar code" labeling systems could provide specific labeling of thousands of oligonucleotides. The beard.or "bar code" could be made of a magnetic, optical, or conductive type of media, much like CD or disk drive media currently used. These micro bar codes would be synthesized as cylinders between 10–50 nm around and no longer than 200 nm. The fabrication process, sputtering, would use technology common to the semiconductor industry. The sputtering process can be utilized to deposit layers of almost any substance on a surface with a very precise, controlled thickness. Alternating layers of two different substances can be generated to create the bar code, then cut into cylinders. These layers of material would be of distinguishable type i.e., clear vs. opaque for optical detection or conductive vs. insulating for detection by conductivity.

Under some conditions, it is also possible that fluorescent dyes may be detected at a single molecule level. Multiple fluorochromes currently exist and are commonly used in flow cytometry. These fluorescent markers can be covalently attached to bead resins to generate distinct bead labels.

Microspheres with multiple fluorescent molecular fillings, different materials, surface texture, surface patterns, etc. can be utilized as identification tags. Probes would be covalently bound to oligonucleotide probes during oligonucleotide synthesis. Fluorescently filled microspheres are currently available from Molecular Probes, Inc. and other companies. Microspheres as small as 20 nm diameter polystyrene beads are currently available.

Spectral absorption labels may also be used. A possible methodology for detection would be to mix into the bead polymer different materials that absorb and pass different spectra of light. Each different type of bead could be detected by passing a multi-spectral light though the bead and detecting which spectra are absorbed.

A complete set of all possible probes of a given length ($4^N$, where N is the length) or a subset of this complete set may be used in the hybridization step. Probes of differing lengths may also be used. A large number of probes may be synthesized in a small number of reactions. For example, a complete set of all possible 10-mers (about 1 million probes) may be synthesized as follows. 1000 5-mers, each uniquely associated with a 10-digit DNA bar code, are synthesized in 1000 reactions and mixed. The mixture is divided into 1000 aliquots which then undergo 1000 reactions, during which the informational length of the probe is extended by an additional 5 nucleotides and the 10-digit bar code is extended by a further 10 digits, to form 1 million uniquely tagged 10-mers synthesized in only 2000 reactions.

To make a mixture of oligonucleotides in small number of reaction and to have each different sequence tagged with a unique tag a combinatorial addition of bases and tag units has to be performed. Example of making all 6-mers (4096) in 6×4 reactions. In the first set of four reactions, four different unit tags are coupled for each of four nucleotides. These unit tags may be four different monomers or for example four dimers of two different monomers premade or synthesized in two sets in these four reactions. The products from four reactions are mixed and approximately equimolary split in second set of four reactions. In each of these reactions, one of the nucleotides is coupled to form a dimer, and a unique unit of tag is linked to previous unit of tag. The result in one of four reactions may be represented as T1-T1-A-A, T1-T2-C-A, T1-T3-G-A and T1-T4-T-A, where each different tag T is unique or may represent a unique oligomer, e.g., T1=t1-t1, T2=t1-t2, T3=t1-t3, T4=t1-t4.

Conventional labeling of probes that requires detection of multiple molecules is not required according to the present invention, but if desired, oligonucleotide probes may be labeled with fluorescent dyes, chemiluminescent systems, radioactive labels (e.g., $^{35}S$, $^{3}H$, $^{32}P$ or $^{33}P$) or with isotopes detectable by mass spectrometry, by any of a variety of methods that are well known in the art.

Hybridization Reaction

The number and type of probes that are used in each solution-based hybridization reaction depends on the detection/tagging resolving power of the reader, the statistics of informative pools (or other pools) for probes having different sequences that cannot be discriminated by the reader, and the SBH application (e.g., whether de novo sequencing, resequencing or genotyping is desired). A complete set of all possible probe sequences of the same length may be used, or only a portion of this complete set may be used. Alternatively, probes of differing length may be used. The only requirement is that there be overlap among the sequences of the information region of some, not necessarily all, of the probe molecules.

According to the present invention, purely statistical factors suggest that the reader should detect about 5–10 of the probe molecules that hybridize to the target nucleic acid. Taking into account the fact that only a certain fraction of available probe molecules that could hybridize will actually hybridize to the target nucleic acid, the fact that the reader is not expected to read all of the probe molecules that hybridize to the target nucleic acid, and other additional factors such as the use of degenerate ends, ideally each information region sequence is represented by about $10^4$ or less, or $10^5$ or less probe molecules, although about 5000 or less, or about $10^3$ or less or about 500 or less, or about $10^2$ or less may suffice.

Before positive probes are selected or detected, methods known in the art can be used to eliminate mismatched target:probe hybrids, e.g., enzymes specific to mismatched regions of hybridization or chemicals that degrade mismatched hybrids.

Hybridization Conditions

Hybridization and washing conditions may be selected to detect substantially perfect match hybrids (such as those wherein the fragment and probe hybridize at six out of seven positions), or may be selected to permit detection only of perfect match hybrids by the use of more stringent hybridization conditions.

Exemplary conditions according to the following invention include conditions which produce,on average, more probe:target hybridization with probe molecules which are perfectly complementary to the target nucleic acid in the information region of the probe molecules than with probe molecules which are mismatched in the information region. Such conditions may allow discrimination of probe molecules which are perfectly complementary to target from those which are not.

Suitable hybridization conditions may be routinely determined by optimization procedures or pilot studies. Such procedures and studies are routinely conducted by those skilled in the art to establish protocols for use in a laboratory. See e.g., Ausubel et al., Current Protocols in Molecular Biology, Vol. 1–2, John Wiley & Sons (1989); Sambrook et al., Molecular Cloning A Laboratory Manual, 2nd Ed., Vols. 1–3, Cold Springs Harbor Press (1989); and Maniatis et. al., Molecular Cloning: A Laboratory Manual, Cold Spring Harbor Laboratory Cold Spring Harbor, N.Y. (1982), all of which are incorporated by reference herein. For example, conditions such as temperature, concentration of components, hybridization and washing times, buffer components, and their pH and ionic strength may be varied. See also Int'l Publication No. WO 98/31836 published Jul. 23, 1998 and WO 99/09217 published Feb. 28, 1999, both of which are incorporated herein by reference.

Selection of Positive Probes

The subset of positive probes, i.e., those probes which have hybridized to the target polynucleotide during the hybridization reaction step, may be selected or optionally separated out from the initial pool of probes in a variety of different ways. For example, double-stranded probe:target hybrids that have hybridized to target nucleic acid can be selected from single-stranded negative probes by enzymatic digestion of single-stranded or mismatched probes using enzymes that recognize single-stranded nucleic acid or mismatched hybridized nucleic acid (if all of the single-stranded nucleic acid is digested, then the remaining nucleic acids are the positive probes). Any suitable exonuclease or endonuclease known in the art may be used; exemplary enzymes include mung bean nuclease, exonuclease VII, Bal31 nuclease and nuclease S1 (which not only degrades single stranded ends but may also cleave at small mismatched gaps). See generally, Maniatis, *Molecular Cloning: A Laboratory Manual*, Cold Spring Harbor Laboratory, Cold Spring Harbor (1982).

Alternatively, double-stranded probe:target hybrids can be separated from single-stranded nucleic acid by any procedure known in the art, such as hydroxyl apatite chromatography, gel electrophoresis, or other gradients.

In yet a further embodiment, the target nucleic acid or the probes can be associated with a separator tag, e.g., biotin or fluorescein, and positive probes that have hybridized to the target nucleic acid can be selected by using the separator tag to separate the target nucleic acid from the solution, e.g., with avidin or an anti-fluorescein antibody. Any suitable binding partner known in the art can be used as a separator tag, e.g., biotin-streptavidin, antigen-antibody binding partner pairs (such as FLAG tag-antibody), histidine tag-nickel, calmodulin binding peptide-calmodulin, dihydrofolate reductase-methotrexate, maltose binding protein-amylose, chitin binding domain-chitin, cellulose binding domain-cellulose, and glutathione-S-transferase (GST)-glutathione, and other binding partner pairs known in the art.

As another example, when a Format 3-like type SBH method is used, in which two sets of shorter probes are combinatorially connected (ligated) to simulate a much larger set of longer probes, two shorter probes are ligated when they hybridize contiguously on the target polynucleotide. If each set of shorter probes is commonly tagged and a different common separator tag is used for each set, e.g., tag A for one set and tag B for the second set, the set of ligated positive probes will have both tag A and tag B but the negative unligated probes will only have one tag (either tag A or tag B). These separator tags thus allow separation of the positive probes in a consecutive two-step process.

In one specific embodiment, a set of 8-mers tagged with biotin and a set of 9-mers tagged with fluorescein are used in the hybridization reaction; probes that hybridize contiguously to the target form positive 17-mer probes tagged with both biotin and fluorescein. The 17-mers can then be separated from the solution by contacting the solution first with support-bound avidin followed by a wash to remove unbound probes and target, and then contacting the solution with support-bound anti-fluorescein antibody, followed by a wash to remove unbound probes (or vice versa).

Readers Used to Detect Positive Probes

Different types of readers may be used to detect probes that hybridize to the target nucleic acid under conditions that allow discrimination of perfectly complementary probes from mismatched probes. The requirements for a reader useful according to the present invention are: 1) ability to detect individual oligonucleotide probes at a molecular level and discriminate them from other oligonucleotide probes (either by determining the probe sequence itself or by detecting one, two or more identification tags associated with the probe); 2) capacity to discriminate a large number (hundreds or thousands) of different oligonucleotides; and 3) sufficient detection speed (using one or many integrated detection channels) to be able to perform statistical sampling sufficient for detecting all positive oligonucleotide probes resulting from the hybridization reaction step. In contrast, conventional detection methods using, e.g., radioisotope labeling require the presence of hundreds or thousands of positive probes before a detectable signal is generated.

If the probe molecule contains an identification tag, preferably the identification tag is detected by the reader without cleaving the tag from the probe. In addition, preferably the detection step takes place in solution. Most preferably, many integrated detection channels/readers are used to improve detection speed by parallel processing.

Suitable readers include readers based on nanopore channels, in which the associated identification tag or the probe sequence itself is read as each probe molecule passes through or over the channel. Other suitable readers include readers based on molecular imaging, in which microscopy at the molecular level allows the discrimination of identification tags. Any other sensor-based method known in the art may be useful according to the present invention if it fulfills the general criteria set forth above.

One preferred reader is based on detection of electrical or other responses at a small pore when an oligonucleotide molecule or its associated tag passes through or over the pore. See, e.g., Church et al., U.S. Pat. No. 5,795,782, incorporated herein by reference, and related publications. As described therein, the molecules can be induced to cross over or through the pore, e.g., by a polymerase or other template-dependent polymer replicating catalyst linked to the pore or located close to the pore, or by a voltage gradient or electric field (i.e., electrophoresis). See also the related publication Meller et al., *Proc. Nat'l Acad. Sci.*, 97:1079–1084 (2000), incorporated herein by reference.

The size of these nanopore channels depends on the types of molecules to be detected and may vary without affecting the mode of detection; the channel should be large enough to accommodate the probe molecule and any associated identification tag, yet should be small enough so that the passage of the probe molecule has a detectable effect on the electrical or other response of the channel. Exemplary sizes include pores ranging from about 1 nm to about 100 nm or preferably about 3 to about 30 nm in diameter. In comparison, the diameter of a nucleotide is typically about 0.3 nm.

Instead of pores, instruments based on various types of gates or channels may be used to read the probe molecules or their associated identification tags as they pass through or pass by. Two layers of (identical or different) pores may be used to read 5' and 3' tags of the probe.

When the oligonucleotide probes are not modified or tagged, discrimination of the natural nucleotide bases in the probes may be used to identify the probe. It may be more difficult to discriminate among all four bases [adenine (A), guanine (G), thyrmidine (T) and cytosine (C)] individually than it is to differentiate A and G (two relatively large purine nucleotides) from T and C (two relatively small pyrimidine nucleotides). For detection of probes according to the present invention, it is not necessary to identify all four bases. For example, differentiation between purines and pyrimidines may be sufficient when probes in the form of PyPuPyPuPyPu, etc. are used. The 5' or 3' end oligonucleotide sequence may also be used in this manner to form a digital bar code.

As another example, when multicolor optical immunolabels based on metallic plasmon-resonant nanoparticles are used as identification tags for the probes, an optical imaging reader may be used to detect the illumination as described in Schultz et al., *Proc. Nat'l Acad. Sci.*, 97:996–1001 (2000), incorporated herein by reference.

Alternatively, chemical sensors based on individual single-walled carbon.nanotubes (SWNTs) have been used to detect small concentrations of toxic gas molecules and may be used to detect the presence of molecules used as identification tags. See, e.g., Kong et al., *Science*, 287:622–625 (2000), incorporated herein by reference, which reports that the electrical resistance of individual semiconducting SWNTs (of a diameter of approximately 1.8 nm) change by up to three orders of magnitude within several seconds of exposure to $NO_2$ or $NH_3$, molecules at room temperature.

When Format 3-like SBH is used, the positive probes (a ligated combination of two shorter probes) may be discriminated from the negative (unligated) shorter probes on the basis of length or by the presence of two identification tags. In this embodiment, the positive probes (i.e., probes that hybridize under appropriate conditions to the target nucleic acid) need not be separated from the negative probes.

The subset of probes scored as positives may be further statistically analyzed to remove false positives from the subset or to add false negatives to the subset. For example, the likelihood of probe X being a true positive may be determined by comparing the frequency of positive scores of probes which have one base difference from probe X's sequence. Probes with one base difference from probe X should score positive with a certain frequency if probe X is a true positive.

Counting the number of probes having the same information region produces a measure of the extent of hybridization and is especially useful for statistical analysis of overlapped probe sequences.

Exemplary Applications

Although theoretically all possible probes can be used in a single hybridization reaction, the number of probes used in a single hybridization reaction may be practically limited by the number of available unique identification tags. If the informative pool methodology is used, each probe need not be uniquely labeled, as a common tag for the pool can suffice. The number of probes used, the number of identification tags used and the number of hybridization reactions for optimal use of the present methods may vary. Exemplary SBH applications that require very large number of probes include the following:

(1) For human and other complex genome resequencing: $3 \times 10^{10}$ informative pools of 32 20-mers may be scored in 3000 hybridization reactions, each of which has a multiplex of $1 \times ^7$ informative pools, requiring the capacity to discriminate 10 million oligonucleotide probes;

(2) For genotyping one million single nucleotide polymorphisms (SNPs) in an individual human genome: 10 million probes may be needed (1 million sites×2 alleles×5 overlapped probes) and may be used in 1–10 independent hybridization/ligation reactions, depending on the tagging strategy and the selection and grouping of SNPs with different sequence to allow simultaneous detection and distinguishing of SNPs;

(3) For de novo sequencing of 100,000 bases with 17-mers: one million informative pools of 16,384 17-mers may be scored in one single hybridization reaction, or one million informative pools may be scored in 16 reactions (with 65,536 unique tags repeatedly used in each reaction).

All three applications may be carried out using hybridization only, or with probe extension by DNA polymerase by at least one base, or Format 3-like SBH in which two sets of shorter probes are combinatorially connected (ligated) to be the equivalent of a much larger set of longer probes. The latter approach offers additional flexibility in combinatorial probe synthesis (i.e., simultaneous synthesis of many probes with different sequences and unique identification tags in the same reaction vessel).

Probe extension by DNA polymerase by at least one base may be carried out essentially as described in, e.g., Cantor, U.S. Pat. No. 5,503,980, incorporated herein by reference. Briefly, the probe:target hybrid can be extended by a nucleotide, e.g., by adding a labeled nucleotide, such as a ddNTP, and using a polymerase (e.g. a Klenow fragment) to extend the probe molecule. All four nucleotides may be added at once if they are differently labeled or tagged.

An example of Format 3-like probe synthesis and scoring for the above example of de novo sequencing of a 100 kb polynucleotide using a complete set of 17-mers in 16 hybridization reactions is described below.

Each of the required 17-mer probes may be formed by combining a 9-mer probe and 8-mer probe. The 9-mers may be prepared as follows. For example, all 256 possible 4-mers may be synthesized in 256 separate reactions and tagged with 256 unique identification tags, positioned at the 3' end. All of the 4-mers are mixed together and then divided into 64 aliquots, which each undergo reactions to add one of all 64 possible 3-mers, thereby forming all possible 7-mers. Finally, all of the 7-mers are mixed together and divided into 16 aliquots, which each undergo reactions to add one of all 16 possible 2-mers, thereby forming all possible 9-mers (approximately 262,000 possible 9-mers). The 9-mers remain divided into 16 aliquots or pools, each of which is used in each of 16 independent hybridization reactions.

For 8-mers, a mix of all 256 possible 4-mers is made, which then are mixed together and divided to undergo 256 additional reactions to add one of all 256 possible 4-mer to each, and to add at the 5' end one specific identification tag arid one common tag for orientation of oligonucleotide probe during the detection step. All 256 reactions are then mixed to form a pool of all 8-mers.

Instead of using 256 tags for marking 256 4-mers at each end, a smaller number of tags may be used to label one of the two 4-mers that might not be sufficiently distinct in the reading process.

One of the 16 separate pools of 9-mers and a pool of all of the 8-mers is hybridized with the target nucleic acid under appropriate conditions. When the hybridization reaction is completed the ligation products are selected (for example by consecutive binding of separator tags, as described above), and detected by the reader. Its orientation can be defined by the 5' tag from 8-mers (e.g., an anion). In this combination of informative pools and tags a specific signal for a 17-mer is the combination of two signals at both 5' and 3' ends. At each end either a specific 4-mer or 4-mer bar code tag is detected. Every one of 65,536 different combinations of signals represent a unique 4-mer+4-mer and 16,384 different middle 9-mer sequences in each of the 16 pools hybridized in independent reactions, thus forming informative pools of 16,384 17-mers.

For a 100 kb target nucleic acid, only about 200,000 17-mers are positive (1 in 80,000) but each of these 200,000 positive probes should be represented about 10 times to allow a statistical sampling to be representative of all positive probes (resulting in a total of 2 million positive probe molecules). To sample almost all 17-mers, optimally about one million probe molecules are scored, a majority of which will be redundant and will therefore have been confirmed by multiple detection.

Conventional Format 1 and 2 SBH

A. Assay Format

Format 1 SBH is appropriate for the simultaneous analysis of a large set of samples. Parallel scoring of thousands of samples on large arrays may be performed in thousands of independent hybridization reactions using small pieces of membranes. The identification of DNA may involve 1–20 probes per reaction and the identification of mutations may in some cases involve more than 1000 probes specifically selected or designed for each sample. For identification of the nature of the mutated DNA segments, specific probes may be synthesized or selected for each mutation detected in the first round of hybridizations.

DNA samples may be prepared in small arrays which may be separated by appropriate spacers, and which may be simultaneously tested with probes selected from a set of oligonucleotides which may be arrayed in multiwell plates. Small arrays may consist of one or more samples. DNA samples in each small array may include mutants or individual samples of a sequence. Consecutive small arrays may be organized into larger arrays. Such larger arrays may include replication of the same small array or may include arrays of samples of different DNA fragments. A universal set of probes includes sufficient probes to analyze a DNA fragment with prespecified precision, e.g. with respect to the redundancy of reading each base pair ("bp"). These sets may include more probes than are necessary for one specific fragment, but may include fewer probes than are necessary for testing thousands of DNA samples of different sequence.

DNA or allele identification and a diagnostic sequencing process may include the steps of:

1) Selection of a subset of probes from a dedicated, representative or universal set to be hybridized with each of a plurality of small arrays;
2) Adding a first probe to each subarray on each of the arrays to be analyzed in parallel;
3) Performing hybridization and scoring of the hybridization results;
4) Stripping off previously used probes;
5) Repeating hybridization, scoring and stripping steps for the remaining probes which are to be scored;
5) Processing the obtained results to obtain a final analysis or to determine additional probes to be hybridized;
6) Performing additional hybridizations for certain subarrays; and
7) Processing complete sets of data and computing obtaining a final analysis.

This approach provides fast identification and sequencing of a small number of nucleic acid samples of one type (e.g. DNA, RNA), and also provides parallel analysis of many sample types in the form of subarrays by using a presynthesized set of probes of manageable size. Two approaches have been combined to produce an efficient and versatile process for the determination of DNA identity, for DNA diagnostics, and for identification of mutations.

For the identification of known sequences, a small set of shorter probes may be used in place of a longer unique probe. In this approach, although there may be more probes to be scored, a universal set of probes may be synthesized to cover any type of sequence. For example, a full set of 6-mers includes only 4,096 probes, and a complete set of 7-mers includes only 16,384 probes.

Full sequencing of a DNA fragment may be performed with two levels of hybridization. One level is hybridization of a sufficient set of probes that cover every base at least once. For this purpose, a specific set of probes may be synthesized for a standard sample. The results of hybridization with such a set of probes reveal whether and where mutations (differences) occur in non-standard samples. To determine the identity of the changes, additional specific probes may be hybridized to the sample.

In another variation, all probes from a universal set may be scored. A universal set of probes allows scoring of a relatively small number of probes per sample in a two step process without an undesirable expenditure of time. The hybridization process may involve successive probings, in a first step of computing an optimal subset of probes to be hybridized first and, then, on the basis of the obtained results, a second step of determining additional probes to be scored from among those in a universal set.

B. Sequence Assembly

In SBH sequence assembly, K-1 oligonucleotides which occur repeatedly in analyzed DNA fragments due to chance or biological reasons may be subject to special consideration. If there is no additional information, relatively small fragments of DNA may be fully assembled in as much as every base pair is read several times.

In the assembly of relatively longer fragments, ambiguities may arise due to the repeated occurrence in a set of positively-scored probes of a K-1 sequence (i.e., a sequence shorter than the length of the probe). This problem does not exist if mutated or similar sequences have to be determined (i.e., the K-1 sequence is not identically repeated). Knowledge of one sequence may be used as a template to correctly assemble a sequence known to be similar (e.g. by its presence in a database) by arraying the positive probes for the unknown sequence to display the best fit on the template.

Within DNA, the location of certain probes may be interchangeable when determined by overlapping the sequence data, resulting in an ambiguity as to the position of the partial sequence. Although the sequence information is determined by SBH, either: (i) long read length, single-pass gel sequencing at a fraction of the cost of complete gel sequencing; or (ii) comparison to related sequences, may be used to order hybridization data where such ambiguities ("branch points") occur. In addition, segments in junk DNA (which is not found in genes) may be repeated many times in tandem. Although the sequence of the segments is-determined by SBH single-pass gel sequencing may be used to determine the number of tandem repeats where tandemly-repeated segments occur. As tandem repeats occur rarely in protein-encoding portions of a gene, the gel-sequencing step will be performed only when a commercial value for the sequence is determined.

C. Sequencing of Mutants

The use of an array of sample arrays avoids consecutive scoring of many oligonucleotides on a single sample or on a small set of samples. This approach allows the scoring of more probes in parallel by manipulation of only one physical object. Subarrays of DNA samples 1000 bp in length may be sequenced in a relatively short period of time. If the samples are spotted at 50 subarrays in an array and the array is reprobed 10 times, 500 probes may be scored. In screening for the occurrence of a mutation, approximately 335 probes may be used to cover each base three times. If a mutation is present, several covering probes will be affected. The use of information about the identity of negative probes may map the mutation with a two base precision. To solve a single base mutation.mapped with this precision, an additional 15 probes may be employed. These probes cover any base combination for two questionable positions (assuming that deletions and insertions are not involved). These probes may be scored in one cycle on 50 subarrays which contain a given sample. In the implementation of a multiple label color scheme (i.e., multiplexing), two to six probes, each having a different label such as a different fluorescent dye, may be used as a pool, thereby reducing the number of hybridization cycles and shortening the sequencing process.

In more complicated cases, there may be two close mutations or insertions. They may be handled with more probes. For example, a three base insertion may be solved with 64 probes. The most complicated cases may be approached by several steps of hybridization, and the selecting of a new set of probes on the basis of results of previous hybridizations.

If subarrays to be analyzed include tens or hundreds of samples of one type, then several of them may be found to contain one or more changes (mutations, insertions, or deletions). For each segment where mutation occurs, a specific set of probes may be scored. The total number of probes to be scored for a type of sample may be several hundreds. The scoring of replica arrays in parallel facilitates scoring of hundreds of probes in a relatively small number of cycles. In addition, compatible probes may be pooled. Positive hybridizations may be assigned to the probes selected to check particular DNA segments because these segments usually differ in 75% of their constituent bases.

By using a larger set of longer probes, longer targets may be conveniently analyzed. These targets may represent pools of shorter fragments such as pools of exon clones.

D. Identification of Heterozygotes Using SBH

A specific hybridization scoring method may be employed to define the presence of heterozygotes (sequence variants) in a genomic segment to be sequenced from a diploid chromosomal set. Two variations are where: i) the sequence from one chromosome represents a basic type and the sequence from the other represents a new variant; or, ii) both chromosomes contain new, but different variants. In the first case, the scanning step designed to map changes gives a maximal signal difference of two-fold at the heterozygotic position. In the second case, there is no masking, but a more complicated selection of the probes for the subsequent rounds of hybridizations may be indicated.

Scoring two-fold signal differences required in the first case may be achieved efficiently by comparing corresponding signals with controls containing only the basic sequence type and with the signals from other analyzed samples. This approach allows determination of a relative reduction in the hybridization signal for each particular probe in a given sample. This is significant because hybridization efficiency may vary more than two-fold for a particular probe hybridized with different DNA fragments having the same full match target. In addition, heterozygotic sites may affect more than one probe depending upon the number of oligonucleotide probes. Decrease of the signal for two to four consecutive probes produces a more significant indication of heterozygotic sites. Results may be checked by testing with small sets of selected probes among which one or few probes selected to give a full match signal which is on average eight-fold stronger than the signals coming from mismatch-containing duplexes.

Partitioned membranes allow a very flexible organization of experiments to accommodate relatively larger numbers of samples representing a given sequence type, or many different types of samples represented with relatively small numbers of samples. A range of 4–256 samples can be handled with particular efficiency. Subarrays within this range of numbers of dots may be designed to match the configuration and size of standard multiwell plates used for storing and labeling oligonucleotides. The size of the subarrays may be adjusted for different number of samples, or a few standard subarray sizes may be used. If all samples of a type do not fit in one subarray, additional subarrays or membranes may be used and processed with the same probes. In addition, by adjusting the number of replicas for each subarray, the time for completion of identification or sequencing process may be varied.

Signature Analysis with SBH

Obtaining information about the degree of hybridization exhibited for a set of only about 200 oligononucleotides probes (about 5% of the effort required for complete sequencing) defines a unique signature of each gene and may be used for sorting the cDNAs from a library to determine if the library contains multiple copies of the same gene. By such signatures, identical, similar and different cDNAs can be distinguished and inventoried.

Format 3 Sequencing by Hybridization

Format 3 SBH (as well as Formats 1 and 2) is described more fully in, e.g., Int'l Publication Nos. WO 98/31836 published Jul. 23, 1998 and WO 99/09217 published Feb. 28, 1999, incorporated herein by reference. In Format 3, a first set of oligonucleotide probes of known sequence is immobilized on a solid support under conditions which permit them to hybridize with nucleic acids having respectively complementary sequences. A labeled, second set of oligonucleotide probes is provided in solution. Both within the sets and between the sets the probes may be of the same length or of different lengths. A nucleic acid to be sequenced or intermediate fragments thereof may be applied to the first set of probes in double-stranded form (especially where a recA protein is present to permit hybridization under non-denaturing conditions), or in single-stranded form and under conditions which permit hybrids of different degrees of complementarity (for example; under conditions which discriminate between full match and one base pair mismatch hybrids). The nucleic acid to be sequenced or intermediate fragments thereof may be applied to the first set of probes before, after or simultaneously with the second set of probes. A ligase or other means of causing chemical bond formation between adjacent, but not between nonadjacent, probes may be applied before, after or simultaneously with the second set of probes. After permitting adjacent probes to be chemically bonded, fragments and probes which are not immobilized to the surface by chemical bonding to a member of the first set of probe may be washed away, for example, using a high temperature (up to 100 degrees C.) wash solution which melts hybrids. The bound probes from the second set may then be detected using means appropriate to the label employed (which may be chemiluminescent, fluorescent, radioactive, enzymatic or densitometric, for example). Herein, nucleotide bases "match" or are "complementary" if they form a stable duplex by hydrogen bonding under specified conditions. For example. under conditions commonly employed in hybridization assays, adenine ("A") matches thymine ("T"), but not guanine ("G") or cytosine ("C"). Similarly, G matches C, but not A or T. Other bases which will hydrogen bond in less specific fashion, such as inosine or the Universal Base ("M" base, Nichols et al 1994), or other modified bases, such as methylated bases, for example, are complementary to those bases for which they form a stable duplex under specified conditions. A probe is said to be "perfectly complementary" or is said to be a "perfectly match" if each base in the probe forms a duplex by hydrogen bonding to a base in the nucleic acid to be sequenced. Each base in a probe that does not form a stable duplex is said to be a "mismatch" under the specified hybridization conditions.

A list of probes may be assembled where in each probe is a perfect match to the nucleic acid to be sequenced. The probes on this list may then be analyzed to order them in maximal overlap fashion. Such ordering may be accomplished by comparing a first probe to each of the other probes on the list to determine which probe has a 3' end which has the longest sequence of bases identical to the sequence of bases at the 5' end of a second probe. The first and second probes may then be overlapped, and the process may be repeated by comparing the 5' end of the second probe to the 3' end of all of the remaining probes and by comparing the 3' end of the first probe with the 5' end of all of the remaining probes. The process may be continued until there are no probes on the list which have not been overlapped with other probes. Alternatively, more than one probe may be selected from the list of positive probes, and more than one set of overlapped probes ("sequence nucleus") may be generated in parallel. The list of probes for either such process of sequence assembly may be the list of all probes which are perfectly complementary to the nucleic acid to be sequenced or may be any subset thereof.

The 5' and 3' ends of sequence nuclei may be overlapped to generate longer stretches of sequence. Where ambiguities arise in sequence assembly due to the availability of alternative proper overlaps with probes or sequence nuclei, hybridization with longer probes spanning the site of overlap alternatives, competitive hybridization, ligation of alternative end to end pairs of probes spanning the site of ambiguity or single pass gel analysis (to provide an unambiguous framework for sequence assembly) may be used.

By employing the above procedures, one may obtain any desired level of sequence, from a pattern of hybridization (which may be correlated with the identity of a nucleic acid sample to serve as a signature for identifying the nucleic acid sample) to overlapping or non-overlapping probes up through assembled sequence nuclei and on to complete sequence for an intermediate fragment or an entire source DNA molecule (e.g. a chromosome).

Sequencing may generally comprise the following steps:

(a) contacting an array of immobilized oligonucleotide probes with a nucleic acid fragment under conditions effective to allow a fragment with a sequence complementary to that of an immobilized probe to form a primary complex with the immobilized probe such that the fragment has a hybridized and a non-hybridized portion;

(b) contacting a primary complex with a set of labeled oligonucleotide probes in solution under conditions effective to allow a primary complex including an unhybridized sequence complementary to that of a labeled probe to hybridize to the labeled probe, thereby forming a secondary complex wherein the fragment is hybridized with both an immobilized probe and a labeled probe;

(c) removing from a secondary complex any labeled probe that has not hybridized adjacent to an immobilized probe;

(d) detecting the presence of adjacent labeled and unlabeled probes by detecting the presence of the label; and (e) determining a nucleotide sequence of the fragment by connecting the known sequence of the immobilized and labeled probes.

In this embodiment of SBH, ligation may be implemented by a chemical ligating agent (e.g. water-soluble carbodiimide or cyanogen bromide). A ligase enzyme, such as the commercially available T4 DNA ligase from T4 bacteriophage, may be employed. The washing conditions which are selected to distinguish between adjacent versus nonadjacent labeled and immobilized probes are selected to make use of the difference in stability of continuously stacked or ligated adjacent probes.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

What is claimed is:

1. A method of detecting a sequence of a target nucleic acid, comprising:

(a) contacting a target nucleic acid with one or more mixtures of a plurality of oligonucleotide probe molecules of predetermined length and predetermined sequence, wherein each probe molecule comprises an information region and at least two probe molecules have different information regions, under conditions which produce, on average, more probe:target hybridization with probe molecules which are perfectly complementary to the target nucleic acid in the information region of the probe molecules than with probe molecules which are mismatched in the information region, wherein the target nucleic acid is not attached to a support, and wherein the probe molecules are not attached to a support;

(b) detecting probe molecules that hybridize with the target nucleic acid, using a reader capable of detecting a single probe molecule that hybridizes to target nucleic acid; and (c) detecting a sequence of the target nucleic acid by overlapping sequences of the information regions of at least two of the probe molecules contacted with the target in step (a).

2. The method of claim 1 wherein at least two mixtures are contacted simultaneously.

3. The method of claim 1 wherein at least two mixtures are contacted sequentially.

4. The method of claim 1 wherein the mixture of probe molecules comprises at least about 10 probe molecules distinct in their information regions.

5. The method of claim 1 wherein the mixture of probe molecules comprises at least about 100 probe molecules distinct in their information regions.

6. The method of claim 1 wherein the mixture of probe molecules comprises at least about 1,000 probe molecules distinct in their information regions.

7. The method of claim 1 wherein the mixture of probe molecules comprises at least about 10,000 probe molecules distinct in their information regions.

8. The method of claim 1 wherein the probe molecules comprise modified bases.

9. The method of claim 1 wherein multiple probe molecules are associated with identification tags.

10. The method of claim 9 wherein multiple probe molecules each have two identification tags.

11. The method of claim 9 wherein multiple probe molecules having the same information region are each associated with the same identification tag.

12. The method of claim 9 wherein at least two probe molecules having different information regions are associated with different identification tags.

13. The method of claim 9 wherein the probe molecules are divided into pools, wherein each pool comprise at least two probe molecules having different information regions, and all probe molecules within each pool are associated with the same identification tag which is unique to the pool.

14. The method of claim 9 wherein at least one identification tag is a bar code.

15. The method of claim 14 wherein the bar code is based on a property selected from the group consisting of size, shape, electrical properties, magnetic properties, optical properties, and chemical properties.

16. The method of claim 14 wherein the identification tag is a DNA bar code comprising modified bases.

17. The method of claim 14 wherein the identification tag is a molecular bar code.

18. The method of claim 14 wherein the identification tag is a nanoparticle bar code.

19. The method of claim 14 wherein the bar code comprises elements of varying length, each element comprising a preset number of unit tags.

20. The method of claim 1 wherein the target nucleic acid is associated with a separator tag.

21. The method of claim 1 wherein the probe molecules are associated with separator tags.

22. The method of claim 1 wherein before detection step (b), probe molecules that hybridize to the target nucleic acid are separated from probe molecules that do not hybridize to the target nucleic acid.

23. The method of claim 22 wherein probe molecules that do not hybridize to the target nucleic acid are eliminated by enzymatic digestion.

24. The method of claim 1 wherein step (b) further comprises counting the number of times probe molecules having the same information region are detected.

25. The method of claim 1 wherein a reader comprising a nanopore channel is used to detect probe molecules in step (b).

26. The method of claim 25 wherein sensing of electrical responses within or around the nanopore channel is used to detect probe molecules in step (b).

27. The method of claim 25 wherein the reader detects molecular bar codes in step (b).

28. The method of claim 1 wherein the probe molecules are associated with one or more tags that allow identification of 5'/3' orientation of probe molecules during detection step (b).

29. The method of claim 1 wherein the sequence of the probe molecule(s) is detected in step (b).

30. The method of claim 29 wherein at least two probe molecules are associated with identification tags and the identification tags are also detected in step (b).

31. A method of sequencing a target nucleic acid, comprising:

(a) contacting a target nucleic acid with one or more mixtures of a plurality of oligonucleotide probe molecules of predetermined length and predetermined sequence, wherein each probe molecule comprises an information region and at least two probe molecules have different information regions, under conditions which produce, on average, more probe:target hybridization with probe molecules which are perfectly complementary to the target nucleic acid in the information region of the probe molecules than with probe molecules which are mismatched in the information region, wherein the target nucleic acid is not attached to a support, and wherein the probe molecules are not attached to a support;

(b) covalently joining probe molecules that form contiguous probe:target hybrids that are perfectly complementary to the target in the information region of the probe molecules; and (c) detecting covalently joined probe molecules, using a reader capable of detecting the hybridization of a single probe molecule to target nucleic acid.

32. The method of claim 31 further comprising the step of (d) detecting a sequence of the target nucleic acid by overlapping at least two sequences generated by combining sequences of the information region of two probe molecules contacted with target nucleic acid in step (a).

33. The method of claim 31 wherein before detection step (c), covalently joined probe molecules are separated from probe molecules that have not been covalently joined.

34. The method of claim 1 or 18 wherein at least one nucleotide is added to the end of one or:more probe molecules that hybridize to target nucleic acid using a polymerase or active fragment thereof.

35. The method of claim 34 wherein the probe molecules are contacted with a mixture of four different uniquely labeled nucleotides.

36. The method of claim 1 wherein target nucleic acids comprising an entire human genome are contacted with probe molecules.

37. The method of any one of claims 1, 18 or 20 wherein a single nucleotide polymorphism is detected.

\* \* \* \* \*

UNITED STATES PATENT AND TRADEMARK OFFICE
CERTIFICATE OF CORRECTION

PATENT NO. : 6,537,755 B1
DATED : March 25, 2003
INVENTOR(S) : Radoje T. Drmanac It is certified that error appears in the above-identified patent and that said Letters Patent is hereby corrected as shown below:

Column 26,
Line 67, please replace "pool comprise at least" with -- pool comprises at least --.

Column 28,
Line 26, please replace "the step of (d)" with -- the step of: (d) --.
Line 36, please replace "one or:more probe" with -- one or more probe --.

Signed and Sealed this

Twenty-fifth Day of October, 2005

JON W. DUDAS
*Director of the United States Patent and Trademark Office*